US008287567B2

(12) United States Patent
Gazzani et al.

(10) Patent No.: US 8,287,567 B2
(45) Date of Patent: Oct. 16, 2012

(54) DEVICE FOR SECURING A CRANIAL LIMB TO THE CRANIAL TOP AND FOR SIMULTANEOUSLY CLOSING CRANIOTOMY HOLES, AND PROCESS FOR USING IT

(75) Inventors: Igino Romolo Gazzani, Ovada (IT); Moreno Carvani, Ovada (IT); Piero Cavigliasso, Ovada (IT); Giancarlo Guizzardi, Ovada (IT)

(73) Assignee: NTPLAST S.R.L., Ovada (AL) (IT)

( * ) Notice: Subject to any disclaimer, the term of this patent is extended or adjusted under 35 U.S.C. 154(b) by 294 days.

(21) Appl. No.: 12/681,100

(22) PCT Filed: Sep. 15, 2008

(86) PCT No.: PCT/IT2008/000591
§ 371 (c)(1),
(2), (4) Date: Apr. 20, 2010

(87) PCT Pub. No.: WO2009/044421
PCT Pub. Date: Apr. 9, 2009

(65) Prior Publication Data
US 2011/0152623 A1    Jun. 23, 2011

(30) Foreign Application Priority Data
Oct. 1, 2007   (IT) .............................. TO2007A0686

(51) Int. Cl.
*A61B 17/08* (2006.01)
*A61B 17/04* (2006.01)
*A61B 17/84* (2006.01)
*A61D 1/00* (2006.01)
*A61F 2/08* (2006.01)

(52) U.S. Cl. ........................ 606/216; 606/232; 606/324
(58) Field of Classification Search .................. 600/205; 606/104, 71, 213, 215, 216, 217, 218, 232, 606/324; 24/704.2
See application file for complete search history.

(56) References Cited

U.S. PATENT DOCUMENTS
5,916,200 A    6/1999  Eppley et al.
(Continued)

FOREIGN PATENT DOCUMENTS
DE    203 15 612 U1    12/2003
(Continued)

OTHER PUBLICATIONS

Ntplast S.R.L., "Written Opinion of the International Searching Authority and International Search Report," European Patent Office, Jan. 26, 2009 for International Patent Application No. PCT/IT2008/000591.

*Primary Examiner* — Kevin T Truong
*Assistant Examiner* — David Bates
(74) *Attorney, Agent, or Firm* — David A. Farah; Sheldon Mak & Anderson PC

(57) ABSTRACT

A device is described for securing a cranial limb to the cranial top and for simultaneously closing craniotomy holes, comprising: a cortical support riser; first closing means operatively connected to the cortical riser; second closing means adapted to be secured to the cortical riser; and at least one handle removably connected to the cortical riser and adapted to drive the device to take it from its rest position to its operating securing position. A process for using such device is further described.

7 Claims, 5 Drawing Sheets

U.S. PATENT DOCUMENTS

| | | | |
|---|---|---|---|
| 6,537,286 B2 * | 3/2003 | Acampora et al. | 606/151 |
| 7,048,738 B1 * | 5/2006 | Wellisz et al. | 606/70 |
| 7,717,929 B2 * | 5/2010 | Fallman | 606/158 |
| 8,083,782 B2 * | 12/2011 | Ralph et al. | 606/283 |
| 8,197,506 B2 * | 6/2012 | Burke et al. | 606/215 |
| 8,206,425 B2 * | 6/2012 | Khanna | 606/324 |
| 2002/0156475 A1 * | 10/2002 | Lerch et al. | 606/70 |
| 2002/0169455 A1 | 11/2002 | Bannerman et al. | |
| 2003/0176890 A1 * | 9/2003 | Buckman et al. | 606/213 |
| 2003/0229349 A1 | 12/2003 | Wellisz et al. | |
| 2008/0051792 A1 * | 2/2008 | Gilete Garcia | 606/72 |
| 2009/0281568 A1 * | 11/2009 | Cendan et al. | 606/217 |

FOREIGN PATENT DOCUMENTS

| | | |
|---|---|---|
| EP | 1 779 793 A1 | 5/2007 |
| JP | 2003 220071 A | 8/2003 |

* cited by examiner

DEVICE FOR SECURING A CRANIAL LIMB TO THE CRANIAL TOP AND FOR SIMULTANEOUSLY CLOSING CRANIOTOMY HOLES, AND PROCESS FOR USING IT

CROSS-REFERENCE TO RELATED APPLICATION

The present Application is a national stage of International Patent Application No. PCT/IT2008/000591, titled "Device for Securing a Cranial Limb to the Cranial Top and for Simultaneously Closing Craniotomy Holes, and Process for Using It," filed Sep. 15, 2008, which claims priority from Italian Patent Application No. TO2007A000686 filed Oct. 1, 2007, the contents of which are incorporated in this disclosure by reference in their entirety.

BACKGROUND OF THE INVENTION

1. Field of the Invention

The present invention refers to a device, preferably made of biocompatible plastic elastic material, for securing a cranial limb and for simultaneously closing holes obtained for performing the craniotomy. The present invention further refers to a process for using such device.

2. Background Art

As known, the craniotomy, namely the incision and cutting of a bone limb of the cranial top, is the compulsory neuro-surgical procedure for treating any intra-cranial lesion.

The bone limb is obtained by cutting one or more drill holes, according to two preferred procedures. The first one provides that a cutting blade or a perforating device is used applied to the pneumatic drill, that, with free hands, from the key hole detaches the dura mater below and simultaneously etches the bone. The second procedure, instead, provides that the dura mater is dissected, with a curved periosteum-detaching device, from the bone between a drill hole and the other and afterwards, using a guide, by passing a saw wire, which, when pulled upwards at its ends with wide hands, etches the bone one segment at a time.

At the end of the neuro-surgical intervention, after having sutured the dura mater and suspended the edges to the bone, the limb is rested again into the opening and is secured with detached metal or wire staples, passed through small drill holes paired on the free edge of the cranial bone.

It is however clear that a solution of this type generally does not allow an aesthetically acceptable closure, since it is not always able to avoid that the bone limb can project, collapse, get slanted or rotate.

SUMMARY OF THE INVENTION

Object of the present invention, therefore, is solving the above prior art problems, by providing a device for securing a cranial limb to the cranial top that allows correctly ossifying the bone limb to the cranial top edge and simultaneously closing the holes obtained for craniotomy.

Another object of the invention is providing a device that allows having a lower tension on the brain, even if a brain edema occurs after an operation.

In order to prevent such brain edema, a hole has been pre-arranged in the upper part of the device, that can be easily opened with a dedicated instrument, to allow inserting a drainage.

These and other objects are obtained with a device for securing a cranial limb to the cranial top and for simultaneously closing the craniotomy holes as described in claim 1. Further features of the invention are defined in the dependent claims.

BRIEF DESCRIPTION OF THE DRAWINGS

Further objects and advantages of the present invention will be clear from the following description and the attached drawings, provided merely as a non-limiting example, in which.

DETAILED DESCRIPTION OF PREFERRED EMBODIMENTS

Figure 1:
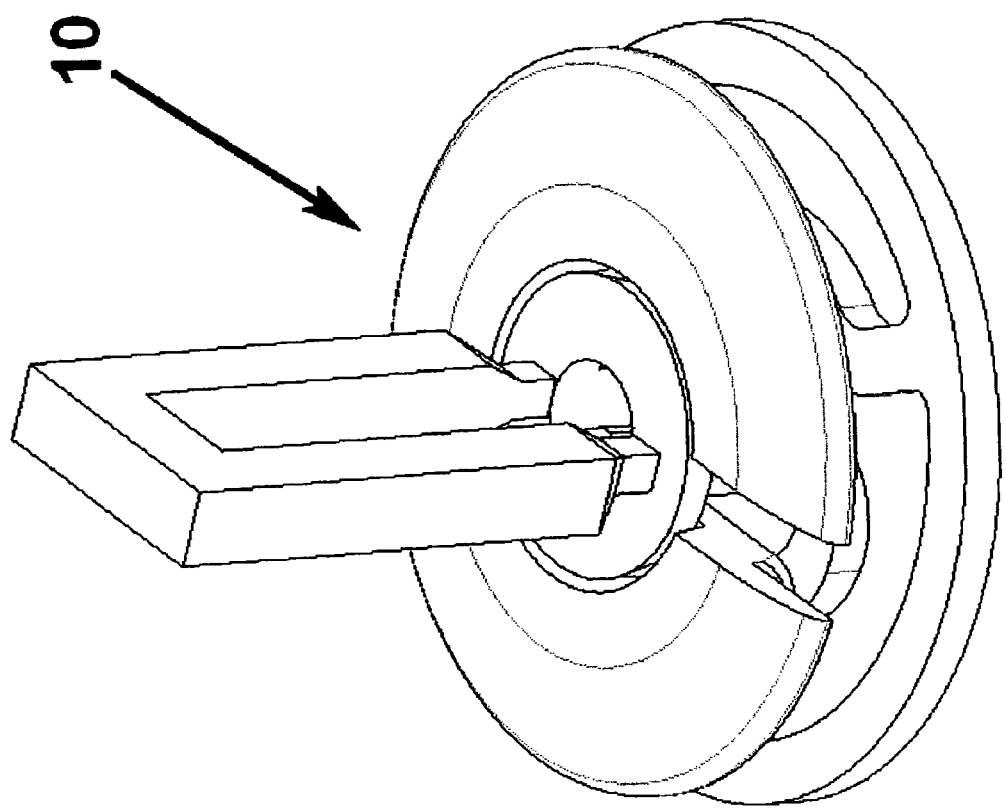
FIG. 1 shows a perspective view of a preferred embodiment of the device for securing a cranial limb to the cranial top and the simultaneous closure of the craniotomy holes according to the present invention.
Figure 2:
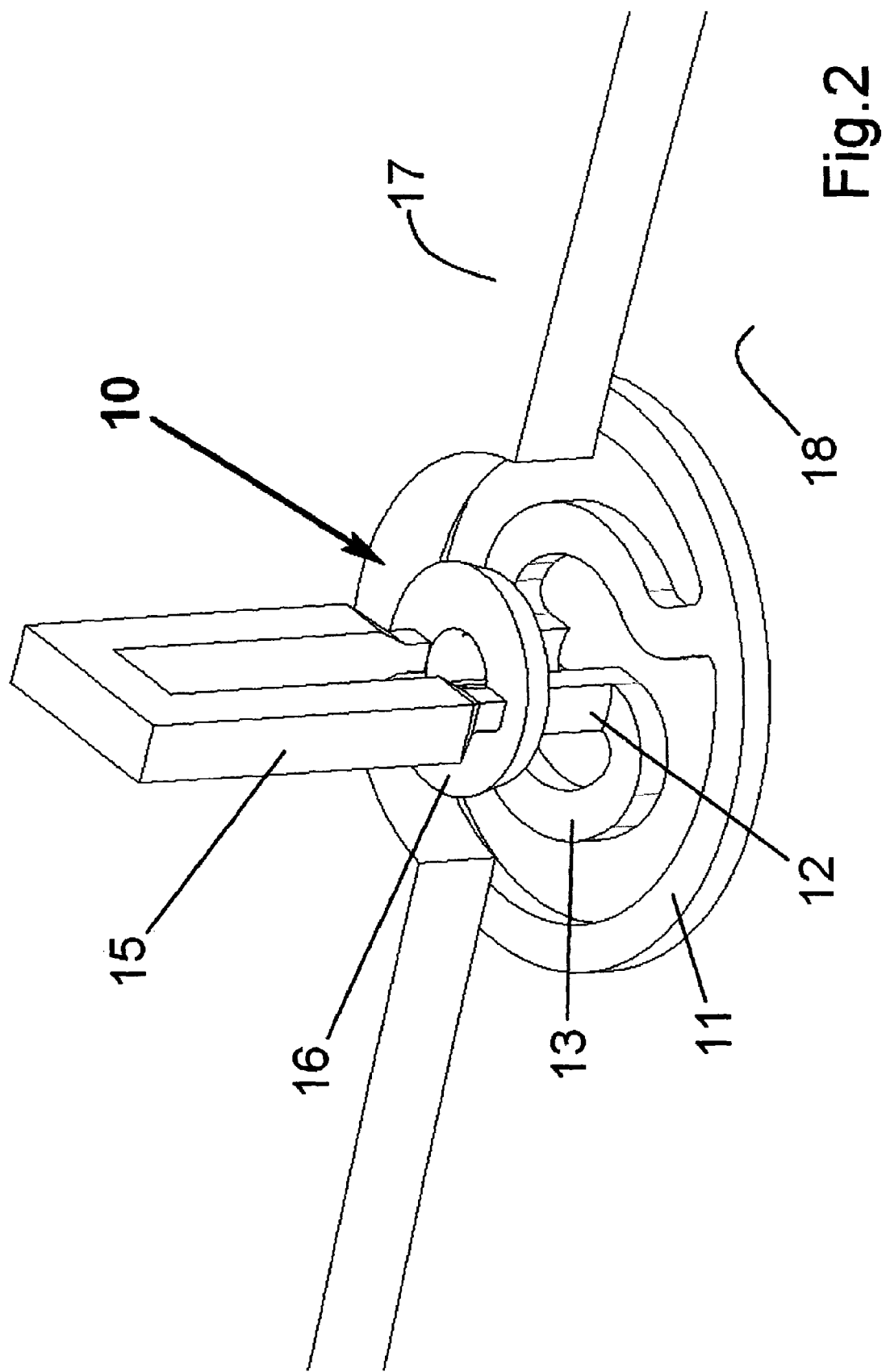
FIG. 2 shows a view of the device of FIG. 1 in a first step of its use.

With particular reference to the cited figures, the device for securing a cranial limb to the cranial top and for simultaneously closing the craniotomy holes, according to the present invention is globally designated with reference number 10.

The device 10 has a lower ring 11, linked to the cortical riser 12 by two elastic arms 13 and an upper plate 14 (FIG. 4), which will have to be inserted into the upper part of the cortical riser 12.

Figure 4:
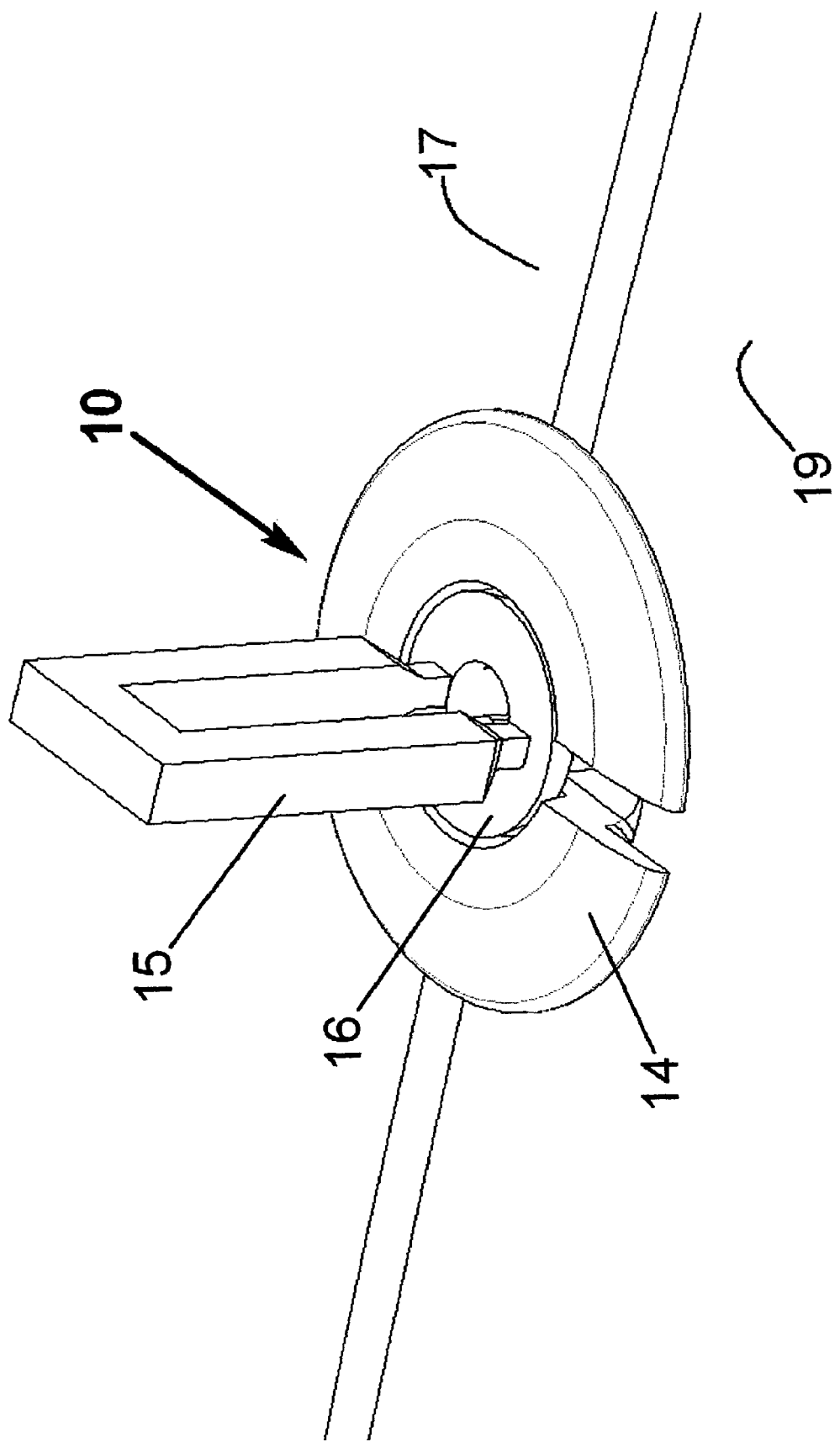
FIG. 4 shows a view of the device of FIG. 1 in a further step of its use.

The cortical riser 12 will be equipped with a handle 15 and a ring 16 for securing 16 that will be used for inserting the upper plate 14 (FIG. 4).

The cortical riser 12, as connection between the lower ring 11 and the upper plate 14, due to the elasticity of the arms 13, allows using only few sizes related to the bone thickness, for example three different sizes, while the circular shape allows any rotation and even the non-parallel positioning of the ring 11 with respect to the plate 14.

Figure 5:
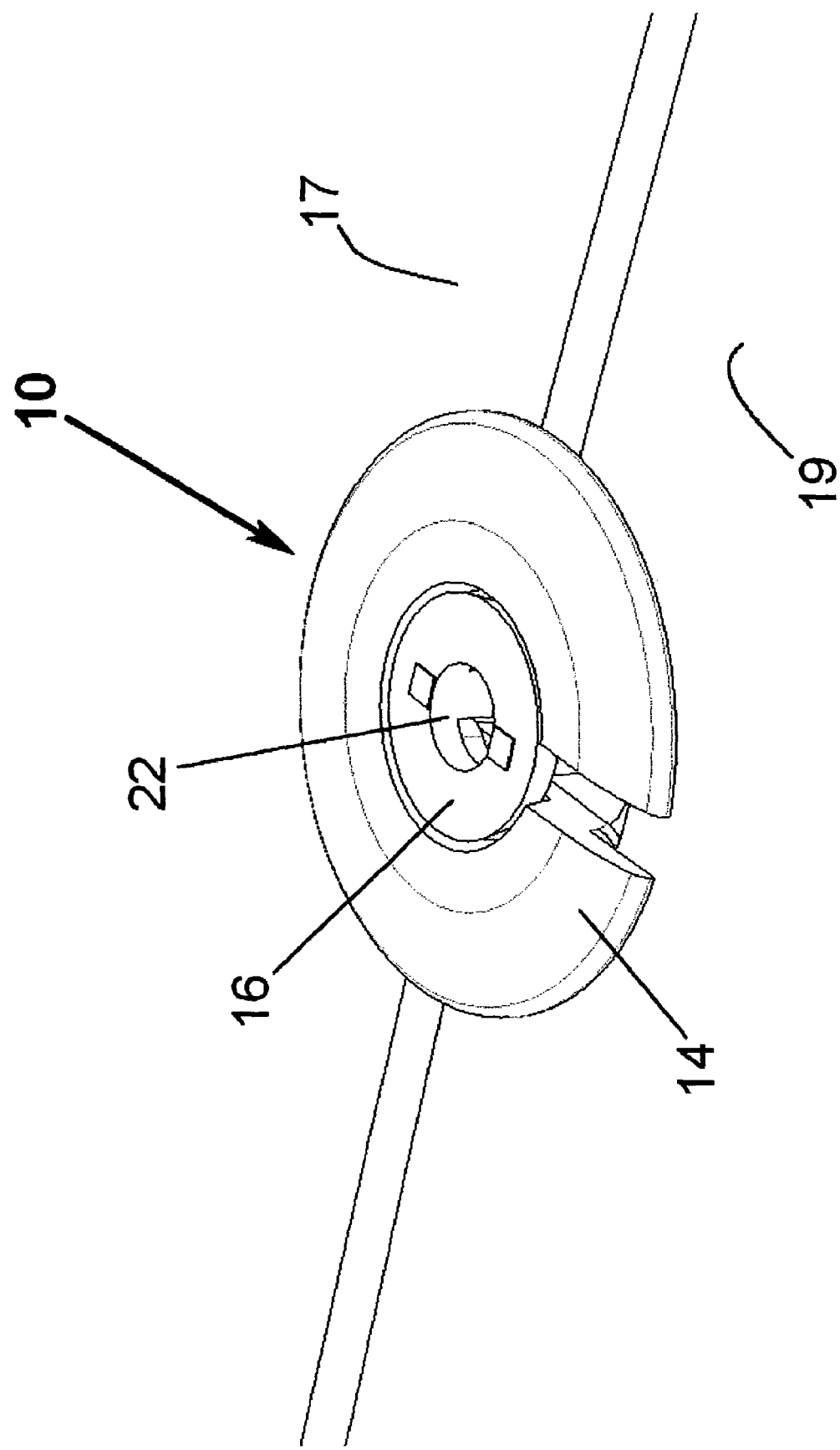
FIG. 5 shows a view of the device of FIG. 1 in the final step of its use.

Finally, even. if it can be seen in all the Figures, in FIG. 5 a hole 22 is expressly shown and better illustrated, which allows passing probes to suck liquids, for extravasations, drainages, etc., such hole 22 being a further advantageous feature of the device 10 of the present invention.

Explaining in more detail the application modes of the cranial securing device 10 of the invention, it can be noted that the instrument operator prepares the amount of devices adapted to secure the craniotomy in its various sizes.

Such operations are performed by choosing the most suitable sizes for the cranial top 17 thickness and the most suitable number of devices 10, depending on the craniotomy largeness and shape.

Moreover, if it will be necessary to insert a drainage, in one of the devices the hole 22 pre-arranged in the securing ring 16 will have to be opened, through suitable drilling pliers (not shown).

The surgeon, with the already assembled catching pliers (not shown), inserts the lower ring 11 in the space between the cranial top 17 and the dura mater 18, so that the cortical riser 12 is at the centre of the hole obtained in the cranial top 17.

Figure 3:
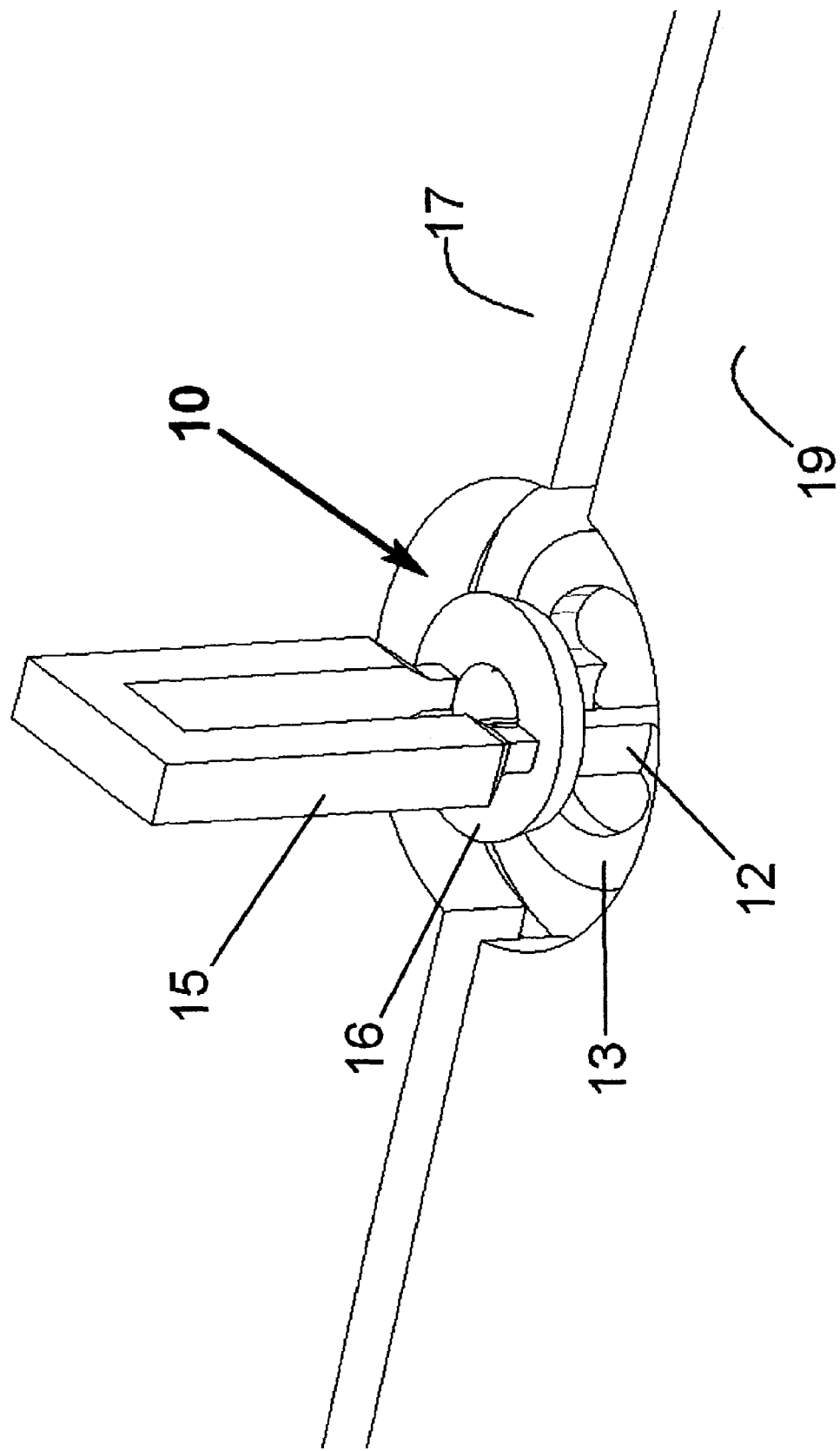
FIG. 3 shows a view of the device of FIG. 1 in a second step of its use.

The bone cover 19 is abutted onto the lower ring 11 of the device 10, as shown in FIG. 3.

Afterwards, the surgeon verifies the correct position of the cover 19 and stretches, by means of the handle 15, the cortical riser 12 and the elastic arms 13 to be able to insert the upper plate 14 into the securing ring 16, like in FIG. 4. Finally, he removes the handle 15 with a scalpel (FIG. 5).

The cranial securing device 10 of the invention is advisable in all craniotomy cases, since its shape and the different sizes in which it can be made, according to the bone thickness, allow keeping the bone limb stretched on board the cranial top, both on the internal and on the external margins, in order to allow the right ossification and to close the holes obtained for the craniotomy.

At the same time, the elasticity of the used biocompatible plastic material guarantees, after the operation, namely when brain edema, and therefore brain swelling, conditions could occur, a lower tension on the brain.

From the above description, the features of the device for securing a cranial limb to the cranial top and for simultaneously closing the craniotomy holes, object of the present invention, appear clear, as well as its resulting advantages.

It is finally clear that numerous variations can be made to the device for securing a cranial limb to the cranial top and for simultaneously closing the craniotomy holes, of the present invention, without departing from the novelty principles contained in the inventive idea.

Finally, when putting the invention into practice, materials, shape and sizes of shown details could be various, according to needs, and they could be replaced with other technically equivalent details.

The invention claimed is:

1. A device for securing a cranial limb to a cranial top and for simultaneously closing a craniotomy hole, the device comprising:
   a) a first section made in a single piece comprising:
      1) a lower ring comprising a central opening;
      2) a cortical riser comprising two struts, each strut comprising a first end and a second end;
      3) a handle connected to both first ends of the struts;
      4) at least two elastic arms, each elastic arm comprising a first end and a second end;
      where the first end of each elastic arm is connected to the lower ring and the second end of the elastic arm is connected to the second end of one strut of the two struts of the cortical riser; and
      5) a securing ring connected to and surrounding the two struts of the cortical riser at the first end of each strut or between the first end of each strut and the second end of each strut;
      where the two struts of the cortical riser define a passage, the passage extending between the securing ring and junctions of the second ends of the struts and the second ends of the elastic arms, and extending through the central opening of the lower ring; and
   b) a second section separate from the first section, where the second section is an upper plate in the general form of an incomplete ring or horseshoe, the upper plate comprising:
      1) an internal circumference and an external circumference;
      2) a central opening defined by the internal circumference and sized to accept the securing ring of the first section; and
      3) a lateral opening extending from the central opening of the upper plate through the external circumference;
      where the lateral opening is sized to permit passage of both struts of the cortical riser within the lateral opening, thereby allowing the second section to join the first section; and
   where both the first section and the second section comprise biocompatible elastic material to allow expansion and contraction of the first section and the second section, and to permit detachment of the handle and any portion of the two struts between the securing ring and the handle using a scalpel.

2. The device of claim 1, where the handle comprises vertical bars, each vertical bar comprising a first end and a second end;
   where the first ends of the two vertical bars are joined by a cross bar; and
   where each second end of each vertical bar is connected to the first end of a strut of the cortical riser.

3. The device of claim 1, where the upper plate further comprises a ledge extending into the central opening of the upper plate configured to accept and stabilize the securing ring.

4. The device of claim 1, where each elastic arm is curvilinear in form.

5. A process for securing a cranial limb to the cranial top and for simultaneously closing a craniotomy hole in the cranial top, the process comprising:
   a) providing the device of claim 1;
   b) inserting the lower ring between the cranial top and dura mater, so that the cortical riser is at a center of the craniotomy hole;
   c) abutting the cranial limb onto the lower ring of the device;
   d) verifying that the cranial limb is correctly positioned;
   e) stretching the cortical riser with the handle above the cranial top and inserting the upper plate onto the cranial top thereby engaging the device to close the craniotomy hole; and
   f) removing the handle from the device.

6. The process of claim 5, where step e) comprises stretching the elastic arms to insert the upper plate into the securing ring.

7. A process for draining the cranial cavity comprising:
   a) creating an opening in the securing ring of a device according to claim 1 that has been placed within a craniotomy hole;
   b) inserting a drainage device or suction device through the opening in the securing ring, between the struts of the cortical riser past the junctions of the second ends of the struts and the second ends of the elastic arms, and through the central opening of the lower ring; and
   c) actuating the drainage device or suction device.

* * * * *